United States Patent
Green, Sr. et al.

[11] Patent Number: 5,868,290
[45] Date of Patent: Feb. 9, 1999

[54] APPARATUS AND METHOD FOR DETECTING VOIDS IN AND DONNING ELASTOMERIC GLOVES

[76] Inventors: David W. Green, Sr.; Ronny Green, both of Rte. 4, Box 4167, Monticello, Fla. 32344

[21] Appl. No.: 845,758

[22] Filed: Apr. 25, 1997

[51] Int. Cl.[6] ............................................. A47G 25/80
[52] U.S. Cl. ................................................ 223/111
[58] Field of Search ........................ 223/111, 78, 79, 223/80

[56] References Cited

U.S. PATENT DOCUMENTS

| | | | |
|---|---|---|---|
| 2,741,410 | 4/1956 | Violette | 223/111 |
| 3,695,493 | 10/1972 | Karr | 223/111 |
| 4,915,272 | 4/1990 | Vlock | 223/111 |
| 5,058,785 | 10/1991 | Rich et al. | 223/111 |
| 5,078,308 | 1/1992 | Sullivan | 223/111 |

*Primary Examiner*—Bibhu Mohanty
*Attorney, Agent, or Firm*—Carnes, Cona & Dixon

[57] ABSTRACT

The present invention is an apparatus which will detect small voids in elastomeric gloves and will also provide an efficient means for donning such gloves. The apparatus includes a first chamber and a second chamber. Each chamber will receive and maintain a glove. A first conduit is coupled to the first chamber and a second conduit is coupled to the second chamber. Located within the first conduit is a first check valve and a second check valve is located within the second conduit. A conventional connector connects the first conduit to the second conduit. Coupled to the conventional connector is a third conduit. This third conduit is sandwich between the connector and a vacuum pump. For enabling each chamber to operate independently and separately from each other, a third check valve is utilized and is located within the third conduit. A power source enables the apparatus to operate while a switch provides the user to activate when desirable. Accordingly, a glove is secured to each chamber to provide for the finger portion to hand downward within each chamber. Once secured, the switch is activated for activating the system. The vacuum is able to operate and will remove air from each chamber. Ambient air is able to flow within the glove and will cause the glove to inflate. A void will not allow the glove to remain inflated.

20 Claims, 8 Drawing Sheets

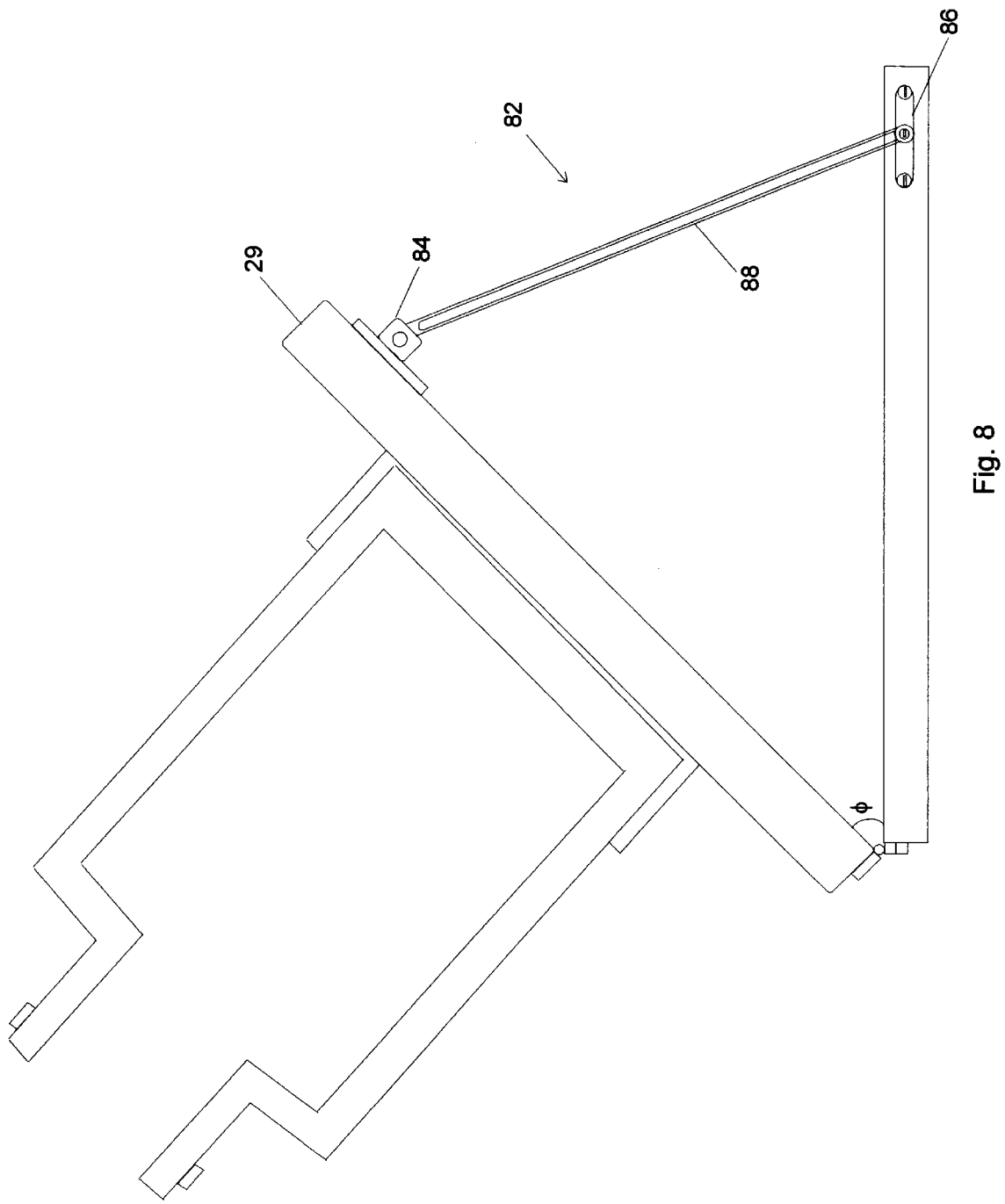

APPARATUS AND METHOD FOR DETECTING VOIDS IN AND DONNING ELASTOMERIC GLOVES

BACKGROUND OF THE INVENTION

1. Field of the Invention

The present invention relates generally to an apparatus which will to detect any defective glove for its removal and more particularly to an apparatus which will inflate the gloves to inherently facilitate its donning while also provide a means of detecting voids in the gloves for their elimination for preventing the transmission of infectious and deadly organisms.

2. Description of the Prior Art

Through the years, health care workers and their patients are becoming more concern as to the sanitary conditions of their working environment. As more research indicates, infectious and deadly organisms can easily be transmitted by way of bodily fluid. To prevent the spread of disease, such as acquired immune deficiency syndrome (AIDS), health care workers and the like will usually wear elastic gloves. These gloves will act as a barrier and will offer protection to the wearer and the patients.

In a typical day, a health care worker, such as nurses, doctors, surgeons, dentists, dental hygienist, or the like, will wear a different and new pair of gloves per patient. Ordinarily, the health care worker will scrub down with an antibacterial soap, dry their hands quickly and then place the gloves thereon, hoping for contamination free gloves. Since these gloves generally assumed a "skin tight" fit when worn, they are inherently difficult to put on, especially if the hand and/or glove is damp. Additionally, adding to the frustrations, air pockets may form at the finger tips requiring several adjustments to release this trapped air. Without an apparatus to assist the user, it is seen that it can be tedious, irritating and time consuming for the donning these gloves.

Once the glove is on, there is no way of indicating if it has any tiny voids in which contaminated fluids can pass therethrough. To avoid this problem some health care professionals will don two gloves for each hand. This extra glove adds to the time wasted for donning the supplemental glove and adds unnecessary cost for the health care professional, insurance companies and patient.

Health care providers are only a few individuals who utilize gloves for protection. Other individuals and professions include, but are not limited to, scientists, researchers, food preparation personnel, and the like, all who recognize the need for protection from products and/or worker contamination.

Accordingly, efforts have been made to aid and assist the health care provider during the procedure of donning gloves. Such a device is disclosed in U.S. Pat. No. 5,078,308 issued to Sullivan. In this patent, there is disclosed an apparatus which operates without internal or external energy sources. The apparatus comprises a cylinder which receives a glove. A tube couples the cylinder to fluid reservoir. The cylinder further includes a one-way check valve which is mounted so that its air inlet communicates with the interior of the cylinder and its air outlet communicates with the ambient environment. For utilizing this device, the user places a glove in the cylinder and makes a fist and quickly inserts and removes the fist from the glove. This will displace the air below the glove forcing it out through the valve. The glove should be in an expanded position due to a partial vacuum which exists below the glove. This apparatus, though useful, does suffer some shortcomings. Since the user must insert a fist into the glove for activating a vacuum, an individual may apply too much pressure and force, inherently causing the glove to be completely removed from the cylinder, an error which is not only undesirable, but irritating as well. Additionally, for those who have large hands, this apparatus may be cumbersome and difficult to master, since their hands, formed as fists, could not properly enter the non-inflated glove. Further, it is questionable if a defective glove can be detected with such a slight vacuum, something that is a necessity in the medical field. In addition, the structure and operation of this device only allows the user to inflate one glove at a time. Such a configuration may require the individual to use the gloved hand for donning the second glove onto the second hand. Since it is desirable for the gloves to remain contact free after leaving the vacuum, the arrangement could contaminate the first glove used in assisting the attachment/release of the second glove.

Yet another device is disclosed in U.S. Pat. No. 4,915,272 issued to Vlock. Vlock discloses a device having a pair of chambers for receiving a glove for each hand. A pump is used to cause a vacuum to exist in the cylinders once the gloves are attached thereto. Though this device is successful, this apparatus is complex as well as cumbersome for utilization. For example, some switches are located within the cylinders, requiring a sterile hand to activate these mechanical devices. Sterilization of the apparatus is virtually impossible since the chambers are at least double or tripled walled. Utilization of the apparatus would require several hours of training and may not offer the best solution, especially in environments where sterilization if of the utmost importance.

Hence it is seen that none of these previous efforts provide the benefits intended with the present invention. Additionally, prior techniques do not suggest the present inventive combination of component elements as disclosed and claimed herein. The present invention achieves its intended purposes, objectives and advantages over the prior art device through a new, useful and unobvious combination of component elements, which is simple to use, with the utilization of a minimum number of functioning parts, at a reasonable cost to manufacture, assemble, test and by employing only readily available material.

SUMMARY OF THE INVENTION

The present invention provides an apparatus which will successfully detect flawed and defective gloves for their removal and elimination. By eliminating these defective gloves provides a means of avoiding a potential transfer of infectious and deadly organism. The apparatus of the present invention will also inflate a glove for rendering a quick and efficient means of donning elastomer gloves in a contamination free environment.

The present invention is simple in design and configuration, yet reliable in operation. This invention comprises two chambers (a first chamber and a second chamber), each having an open top, an enclosed bottom and is of a sufficient size for accommodating an outstretched hand, regardless of hand size. During use, the open top of each chamber is adapted to receive the gloves for providing the fingers of the gloves to be suspended within the chamber and the wrist portion of the glove to be secured to the opened end by way of bending and folding the glove thereon. Due to the natural elasticity of the glove, it will inherently be secured and fastened to the chamber. For aiding the holding power of the gloves, the outer area of each chamber can include a plurality of extenders. When not in use the opened top of each chamber can receive a lid or cover for preventing dust or the like from entering therein.

A first conduit and a second conduit are coupled to the first and second chambers, respectively. Each conduit includes a check valve, providing for a first check valve to be located within the first conduit and a second check valve to be located within the second conduit.

A third conduit, having a third check valve, is coupled to the first and second conduits. Connected to this third conduit is a vacuum pump. Hence, this design and configuration will provide for the vacuum pump to remove air from each chamber. The use of a third check valve in the third conduit will enable the apparatus to operate even if a vacuum created within one of the chambers is broken by a defective glove or by removing a glove from a chamber.

A frame means maintains the chambers and also houses a vacuum pump. This frame means also provides an effective system for transporting the apparatus.

For activating the apparatus of the present invention, a manually operated switch is utilized. The switch can be located on the lower area of the frame means for permitting the switch activated by the foot. This will provide for a more efficient and user friendly apparatus.

Controlling noise and vibration of the vacuum pump is accomplished by insulating the area of the frame means which surrounds the pump. In this fashion, the insulation dampens the vibrations of the pump. The pump is powered via conventional power supply, such as an electrical or battery operated means.

Operation occurs by inserting a glove into either one and/or both chamber so that the thumbs of both gloves face the center and the wrist band of each glove is flipped over the edge of their respective chamber, covering the extenders, if provided. The user activates the apparatus via the switch. The pump creates a vacuum within the interior of each chamber. Atmospheric pressure causes the glove to become inflated. Within a matter of seconds, a flawed glove can easily be detected visually. Should a glove be defective, a vacuum would not hod, thereby failing to hold the flawed glove. With the gloves inflated, the hands are properly inserted therein. The wearer can make a fist and push his fisted hand forward for automatic release. The unique arrangement of the check valves of the present invention enables the chambers to operate independently from each other. Hence, should one glove be defective, the second glove will remain in an inflated position.

Accordingly, it is the object of the present invention to provide for an apparatus for leak checking and donning gloves which will overcome the deficiencies, shortcomings, and drawbacks of prior donning apparatus and methods thereof.

Another object of the present invention is to provide an apparatus for leak checking and donning gloves which includes components which can be disassembled and re-assembly easily and quickly, for efficiently cleaning, sterilizing and disinfecting the apparatus.

Still another object of the present invention is to provide for an apparatus for leak checking and donning gloves in a contamination free environment.

Yet another object of the present invention is to provide for an apparatus for leak checking and donning gloves which can readily accept the user's hand regardless of its size and/or shape.

Yet another object of the present invention, to be specifically enumerated herein, is to provide for an apparatus for leak checking and donning gloves in accordance with the preceding objects and which will conform to conventional forms of manufacture, be of simple construction and easy to use so as to provide an apparatus that would be economically feasible, long lasting and relatively trouble free in operation.

Although there have been many inventions related to apparatus for donning gloves, none of the inventions have become sufficiently compact, low cost, and reliable enough to become commonly used. The present invention meets the requirements of the simplified design, compact size, low initial cost, low operating cost, ease of installation and maintainability, and minimal amount of training to successfully employ the invention.

The foregoing has outlined some of the more pertinent objects of the invention. These objects should be construed to be merely illustrative of some of the more prominent features and application of the intended invention. Many other beneficial results can be obtained by applying the disclosed invention in a different manner or modifying the invention within the scope of the disclosure. Accordingly, a fuller understanding of the invention may be had by referring to the detailed description of the preferred embodiments in addition to the scope of the invention defined by the claims taken in conjunction with the accompanying drawings.

BRIEF DESCRIPTION OF THE DRAWINGS

FIG. 8 is a detail view of the conventional hinge used with the apparatus of the present invention, for providing the chambers to be pivotally secured thereto.

Similar reference numerals refer to similar parts throughout the several views of the drawings.

DESCRIPTION OF THE PREFERRED EMBODIMENTS

Figure 1:
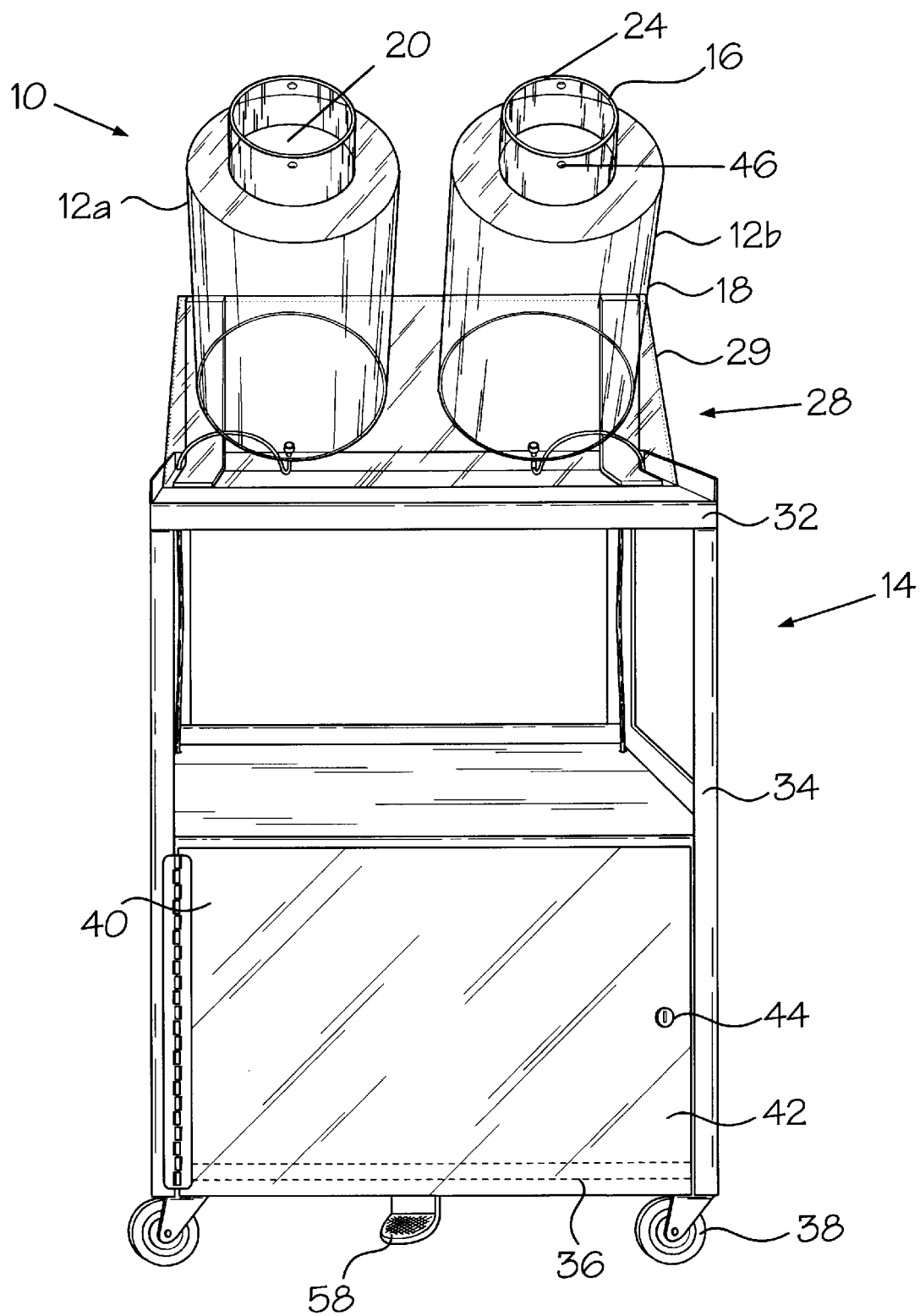
FIG. 1 is a perspective view of the apparatus of the present invention, which is used for leak checking and donning elastomeric gloves.
Figure 2:
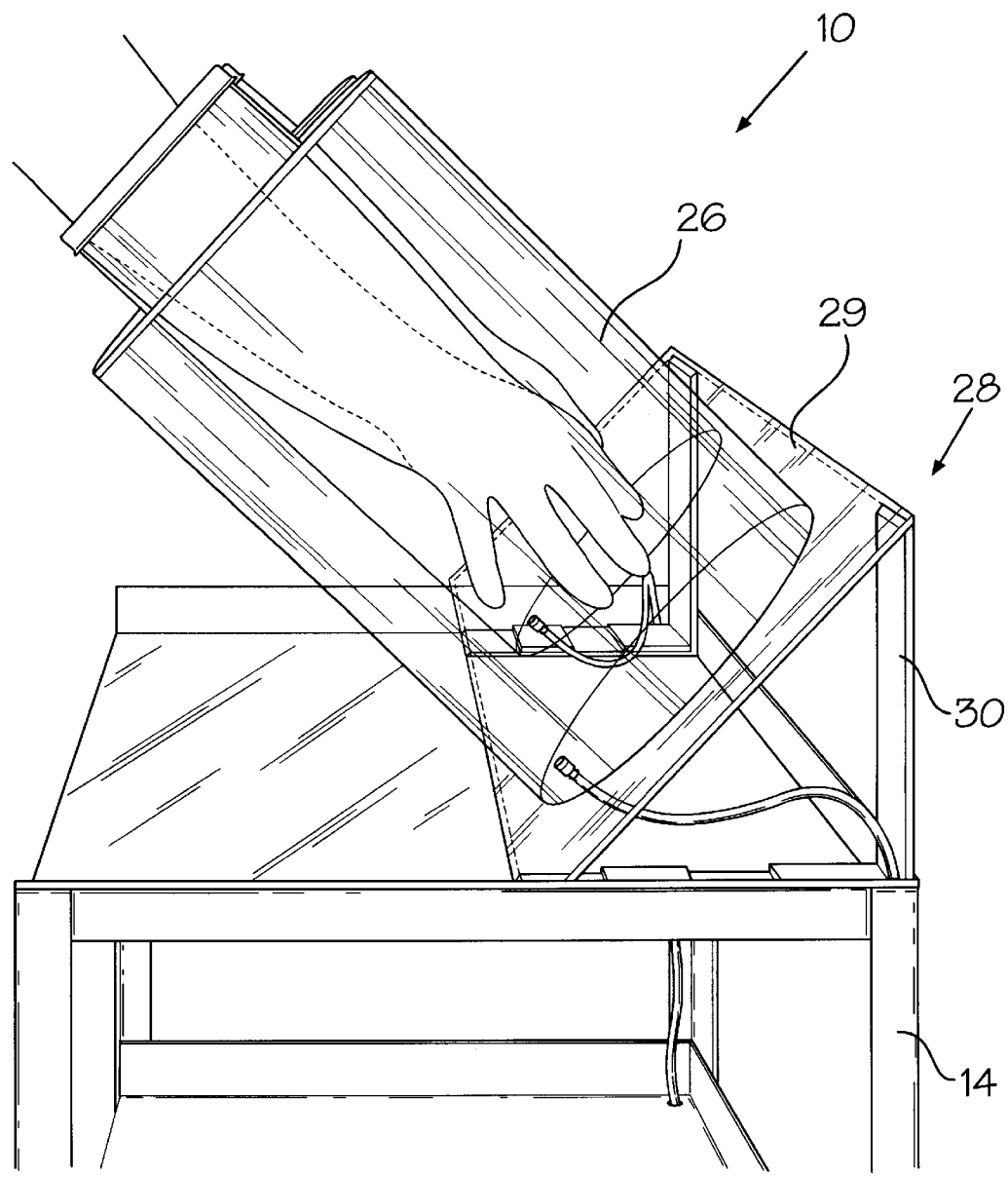
FIG. 2 is a partial side view of the apparatus of the present invention, having a glove secured thereto and which is used for leak checking and donning gloves.
Figure 3:
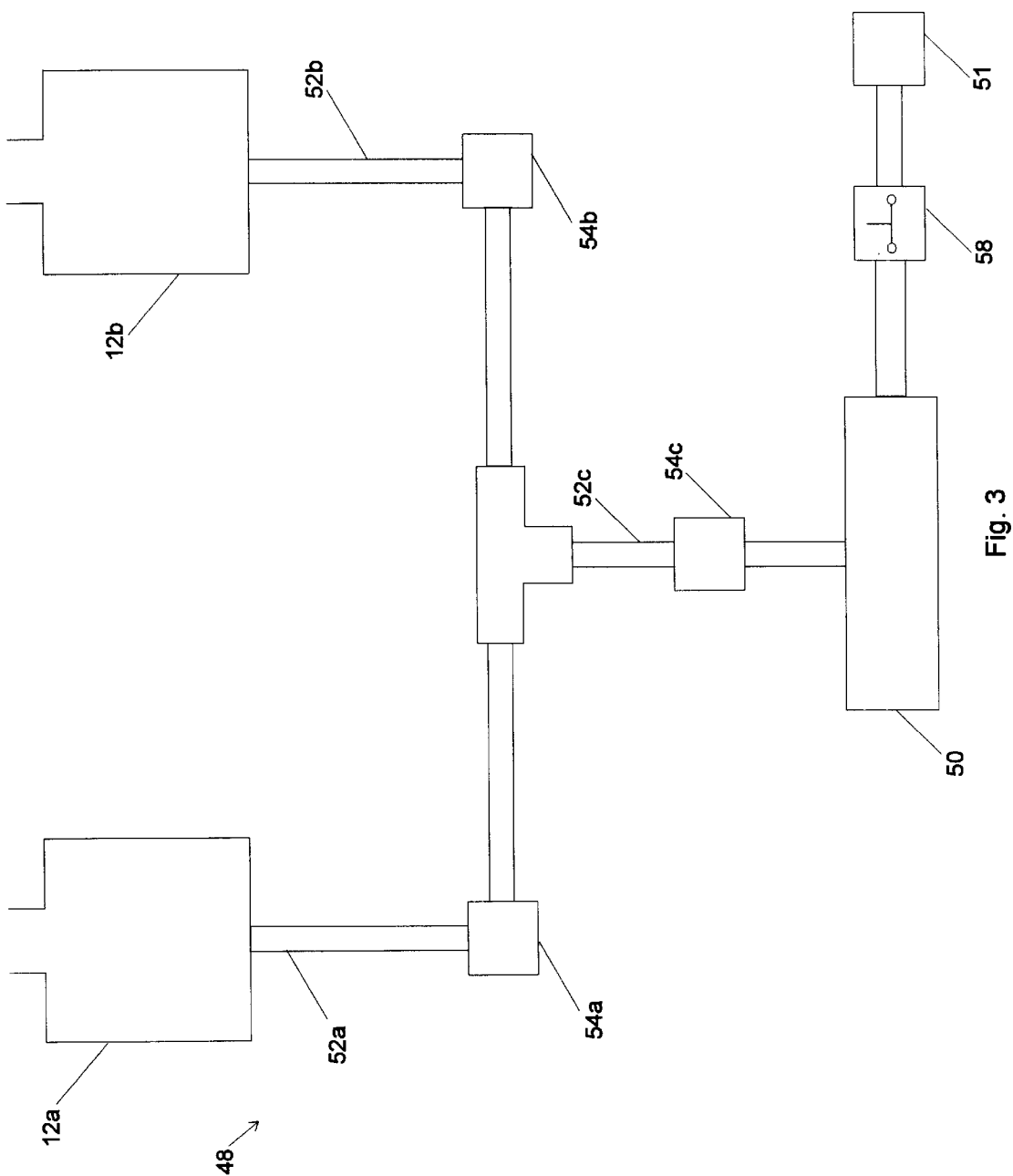
FIG. 3 is a schematic view of the vacuum activating means used in the apparatus of the present invention for checking leaks and for donning gloves.

With reference to drawings, and in particular to FIGS. 1–3 thereof, the apparatus of the present invention will be described. As illustrated in the figures, the present invention 10 is directed towards an apparatus which will inflate a glove for allowing a user to visually determine if the glove includes a small void. If detected, this defective glove can be removed and destroy. Additionally, this apparatus will enable a means for quickly and efficiently donning a glove.

Accordingly, the present invention 10 will provide an apparatus which will inspect for imperfect gloves for their elimination by the user for providing a means of avoiding a potential transfer of infectious and deadly organism, as well as provide a means for donning gloves onto a user, effectively, and in a contamination free environment and simultaneously.

As shown in the drawings, the present invention comprises a first chamber 12a and a second chamber 12b, maintained on a frame means 14. The first chamber 12a and second chamber 12b are identical in shape and size and, additionally, are configured to accept and maintain conventional elastomeric gloves, as illustrated in FIG. 2, but not labeled, commonly used in the medical, scientific, and public food preparatory environment.

Each chamber, 12a and 12b, includes an upper section 16 and a lower section 18. Located in the upper section 16 is an opened top 20 while an enclosed bottom 22 is located in the lower section 18. When not in use, the open top can be covered with a lid or cover.

Each chamber further includes an interior area 24. The design and configuration of the chambers is such that the opened top 20 is adapted to receive the conventional elastomeric gloves for providing the fingers of the gloves to be suspended within the interior area 24 of the chamber. As seen in the drawings, the interior area 24 provides for each chamber to be hollow and empty. An ideal situation for proper sterilization. As further illustrated, in the various views of the drawings, each chamber comprises a singular layer of material. The wrist portion of the glove will be secured to the top edge 24 of the upper section 16 by way of bending and folding the glove thereon. Due to the natural elasticity of the glove, it will inherently be secured and fastened to the chamber. To avoid breakage of the glove, the top edge 24 is smooth in structure. The exterior of the upper section 16 of the gloves can include extenders or bumps 46. These extenders or bumps 46 can aid in the securement of the glove to the chambers.

For accommodating hands of various sizes, the chambers can be constructed in a unique form. As illustrated, the upper section 16 steps in from the lower section 18. This arrangement will increase the size of the interior area 26 of the lower section 18 to provide for a natural increase transition from the area of the glove's wrist to the area of the glove's hand. The increased area will render a chamber which will adequately accept any size hand, even as an outstretched hand or when formed as a fist, both forms required for properly executing the process of donning gloves.

The chambers 12a and 12b are secured to the frame means 14 via a conventional attaching means 28. As shown in the figures, the attaching means includes a base 29 and holding brackets 30. The base 29 maintains the enclosed bottom 22, while the brackets secure the chambers to the frame means. As seen in FIGS. 1 and 2, the attaching means 28 includes a triangular shape to provide for the chambers to be disposed at an acute angle. The angular placement of the chambers can occur at an acute angle or optionally can be displaced perpendicularly with respect to the frame means. To place the chambers perpendicular with respect to the frame means, the triangular attaching means is eliminated and the enclosed bottom is attached directly to the frame means.

Figure 7:
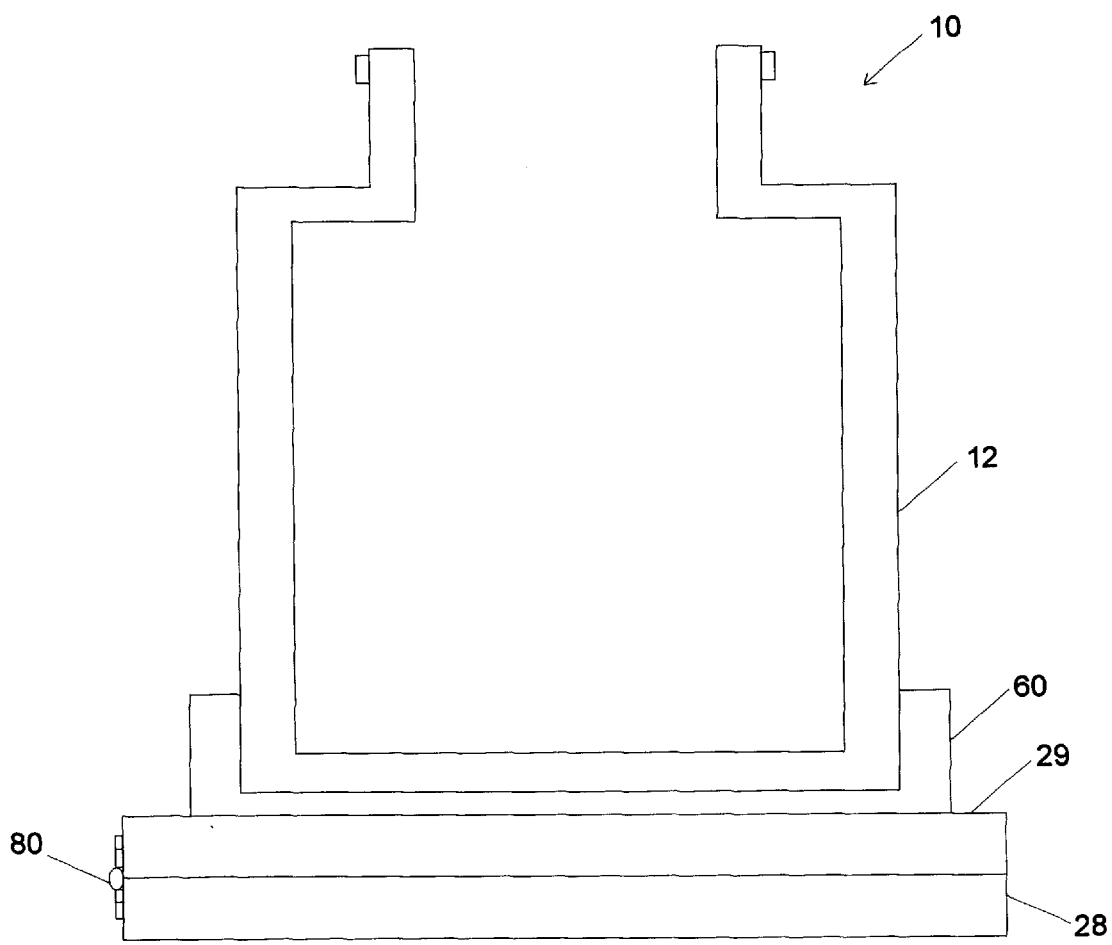
FIG. 7 is a cross-sectional view illustrating the attaching means of the apparatus of the present invention hingedly secured to the frame means.

The angular placement is dependent on the height of the frame means and the location at which the apparatus 10 will be located. For example, perpendicularly displaced chambers (as illustrated in FIG. 7) would be ideal for use with a frame means having a low height. Additionally, perpendicularly displaced chambers provides an apparatus which is ideal for surgery. A perpendicular displacement will assure the prevention of the gloves from touching or contacting the sidewalls of the chambers, thereby providing a sterile means for donning gloves.

For more versatility, the chambers can be secured onto the frame means by way of conventional pivot brackets. Thereby, allowing the user to adjust the angular displacement of the chambers that is suited for their needs. Conventional brackets are disclosed and discussed in further detail in FIGS. 6, 7 and 8.

The frame means 14 is designed to maintain the chamber and to house the vacuum means. As seen in FIGS. 1 and 2, the frame means 14 includes a top flat support surface 32 having legs 34 extending downwardly therefrom. A platform 36 (illustrated in outline in FIG. 1) is under the support surface 32 and to the legs 34. This platform 36 will maintain the vacuum means. For providing a mobile unit, legs 34 can include wheels 38.

Controlling the noise and vibration of the vacuum means can be accomplished by providing covering and walling around the platform. The covering and walling will provide for the frame means 14 to include an enclosed cabinet 40. Accessibility to the vacuum means can obtain by a hingedly or pivotally secured door 42. Preventing tampering of the vacuum means can be attained by proving a lock 44 thereon. Further control of noise and vibration of the vacuum means is achieved by insulating the interior area of the cabinet 40. In this fashion, the insulation dampens the vibrations of the pump.

The vacuum means 48 enables the conventional glove to inflate. This will allow the user to check for any voids or defects and also enables the user to insert their hand therein. In order to accomplish the inflation of the glove, a vacuum is created in each chamber 12a and 12b, separately and independently. Thereby, as air is removed from the chamber, ambient air enters into the interior area of the glove to inherently inflate the attached glove.

For rendering a proper vacuum to exist, the vacuum means comprises a vacuum pump 50, conduits and check valves. As seen in FIG. 3, the vacuum pump 50 is coupled to a conventional power source 51, such as electrical power supply or batteries. Located between the power source and pump 50 is an activation switch 58. A first conduit 52a and a second conduit 52b are coupled to the first and second chambers, 12a and 12b, respectively. Each conduit includes a check valve, providing for a first check valve 54a to be located within the first conduit 12a and a second check valve 54b to be located within the second conduit 12b.

A third conduit 52c, having a third check valve 54c, is coupled to the first and second conduits by a T-shape connector (illustrated, but not labeled). Connected oppositely to this third conduit 52c is the vacuum pump 50. Hence, this design and configuration will provide for the vacuum pump 50 to remove air from each chamber. The use of a third check valve 54c in the third conduit 52c will enable the apparatus to operate even if a vacuum created within one of the chambers is broken by a defective glove or by removing a glove from a chamber.

For activating the apparatus of the present invention, a manually operated switch 58 is utilized. The switch 58 is exteriorly located with respect to the frame means 14. For practicality, it is preferably located on the lower area of the frame means 14 for permitting the switch to be activated by the foot. Such a location will provide for an apparatus which is easy to use and operation.

For utilizing the apparatus of the present invention, the user merely places a pair of gloves in the respective chamber. To secure the glove to the respective chamber, the user inserts the glove into the interior of the chamber so that the thumbs of both gloves face the center and the wrist band of each glove is flipped over the top edge of the upper section. The attachment of the glove to the top edge provides for a hermetic seal to occur between the chamber and the interior area of the apparatus of the present invention. The switch 58 is depressed for activating the vacuum pump, which in turn will cause for proper operation of the apparatus of the present invention.

During operation, the pump 50 removes air from the chambers in order to create a vacuum within the interior area of each chamber. As the vacuum is created, atmospheric pressure causes the glove to become inflated. Within a matter of seconds, a flawed glove can easily be detected visually.

A defective glove, one with hole or the like, will not be able to maintain the inflated state, since the aperture located therein will prevent a vacuum, and inherently cause the glove to deflate. The defective glove can easily be removed and discarded and a new glove can be attached thereto without deactivating the machine. The use of the check valves will allow for the operation of the machine even if a defective gloved is attached to one or both of the chambers. Such an apparatus will render a device which can successfully inflate gloves simultaneously or optionally, one-at-a-time.

Once the gloves are inflated, the hands are properly inserted through the opened top of the upper section of the chamber. The wearer can make a fist and push his fisted hand forward for automatic release of the glove from the top edge of the upper section.

The unique arrangement of the check valves of the present invention allows one directional air flow for enabling the chambers to operate independently from each other. Hence, should one glove be defective, the second glove will remain in an inflated position.

Figure 4:
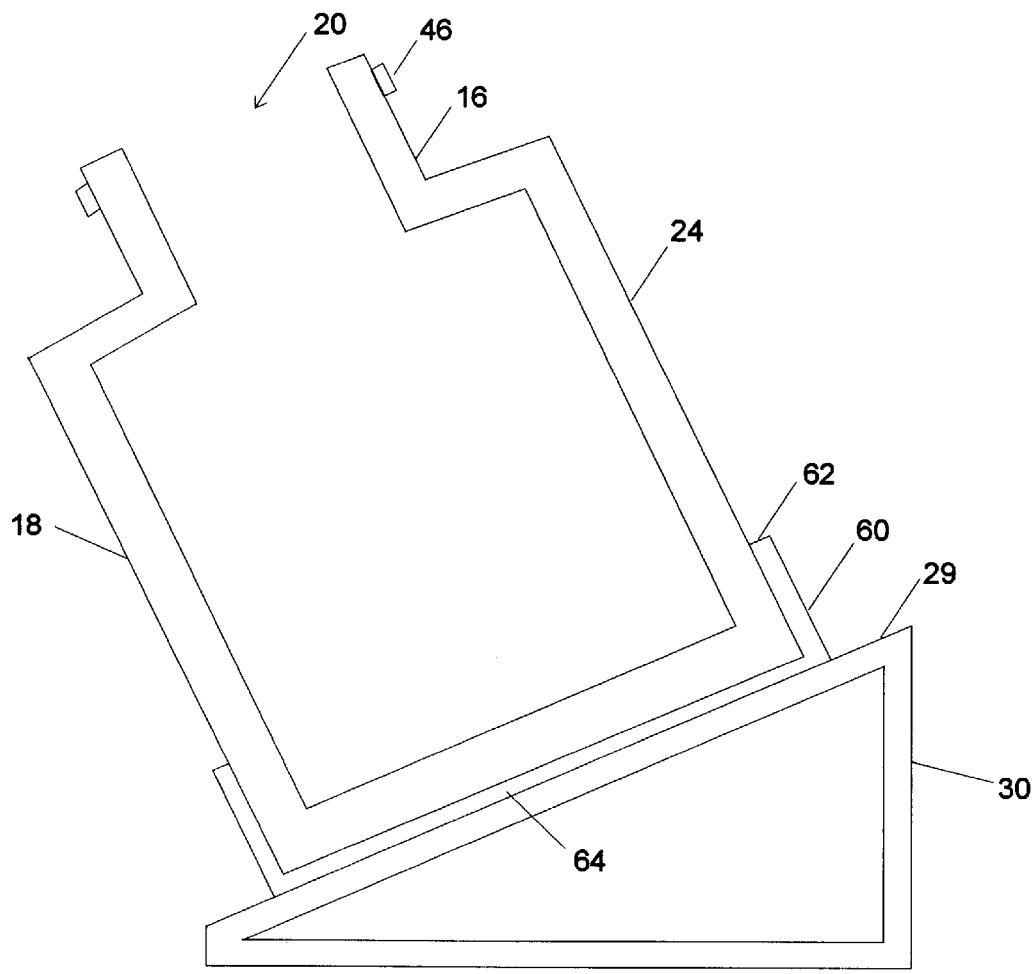
FIG. 4 is a cross-sectional view of an alternative embodiment for the chamber used in the apparatus of the present invention.

The apparatus 10 of the present invention can easily be cleaned and sterilized after each use. Thereby an access means is used to gain access to the interior of the chamber for proper sterilization. This access means, as illustrated and discussed below, can include removing the chamber for cleaning each unit and proper sterilization. For easing cleaning, the chambers 12a and 12b, can be designed to be removably secured to the frame means. This alteration is illustrated in further detail in FIG. 4. As seen in this figure, the chamber, labeled as 12, includes an upper section 16 and a lower section 18. The upper section includes the open top 20 and the exteriorly located bumps 46, while the lower section 18 includes the enclosed bottom 22. Secured to the base 29 of the attaching means 28 is a cup member 60. This cup member 60 includes an open top 62 and an enclosed bottom 64. The open top 62 is adapted to snugly receive the enclosed bottom 22 of the chamber. Thereby, providing a chamber which is removably secured to the frame means and which can properly and efficiently be sterilized. This will provide an apparatus which is well suited for surgery.

Figure 5:
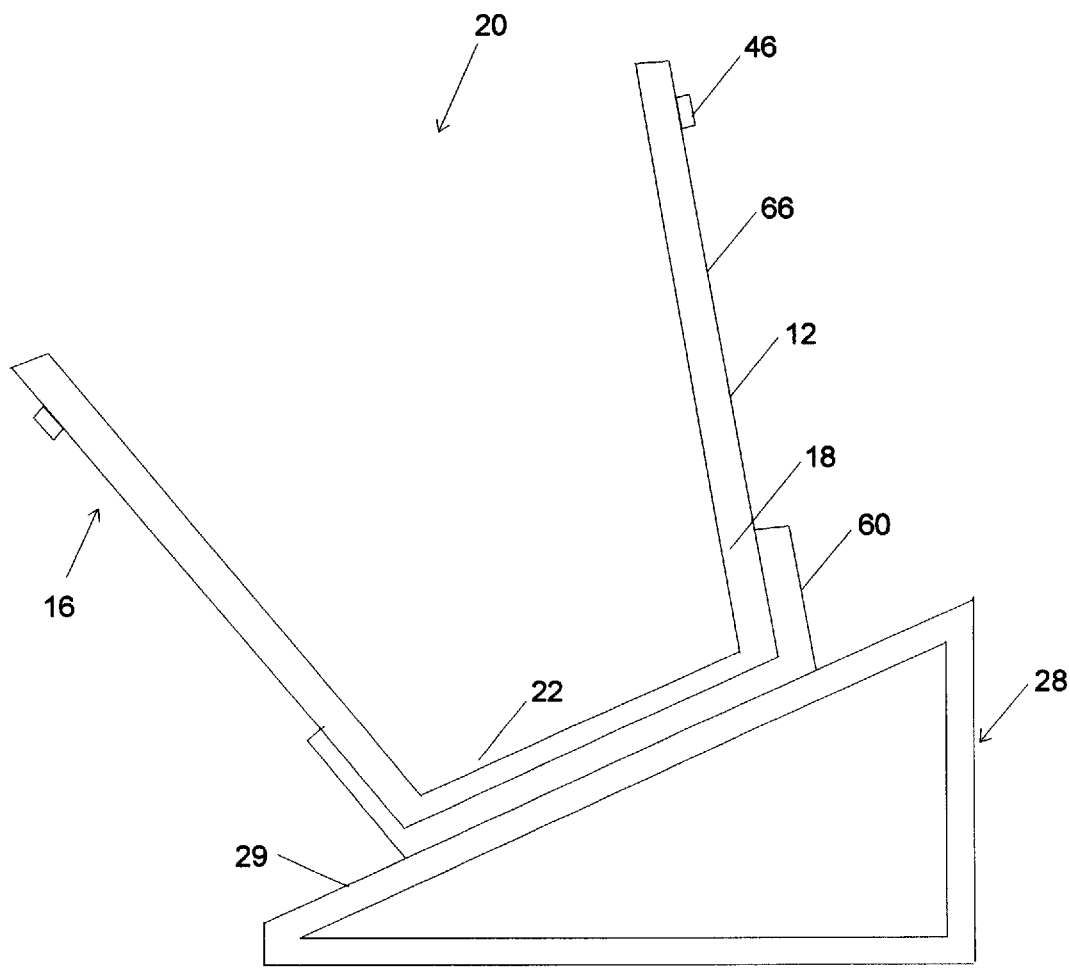
FIG. 5 is a cross-sectional view of an alternative embodiment for the chamber used in the apparatus of the present invention.

Conventional methods for sterilizing in the medical profession includes autoclaving. For allowing the chambers to be autoclavable, the chambers can be re-constructed so as to provide for removable and stackable units. This alteration is illustrated in further detail in FIG. 5. As seen in this figure, the chamber, labeled as 12, includes an upper section 16 and a lower section 18. The upper section includes the open top 20 and the exteriorly located bumps 46, while the lower section 18 includes the enclosed bottom. Secured to the base 29 of the attaching means 28 is a cup member 60. This cup member 60 is similar to structure and design as the cup member discussed and illustrated in FIG. 4.

The chambers further include sidewalls 66 which taper outwardly from the lower section 18 to the upper section 16. Thereby, allowing the enclosed bottom 22 of one chamber to be removably received by the open top 20 of the opposite chamber. This design and configuration allows for the chambers to be stackable.

Figure 6:
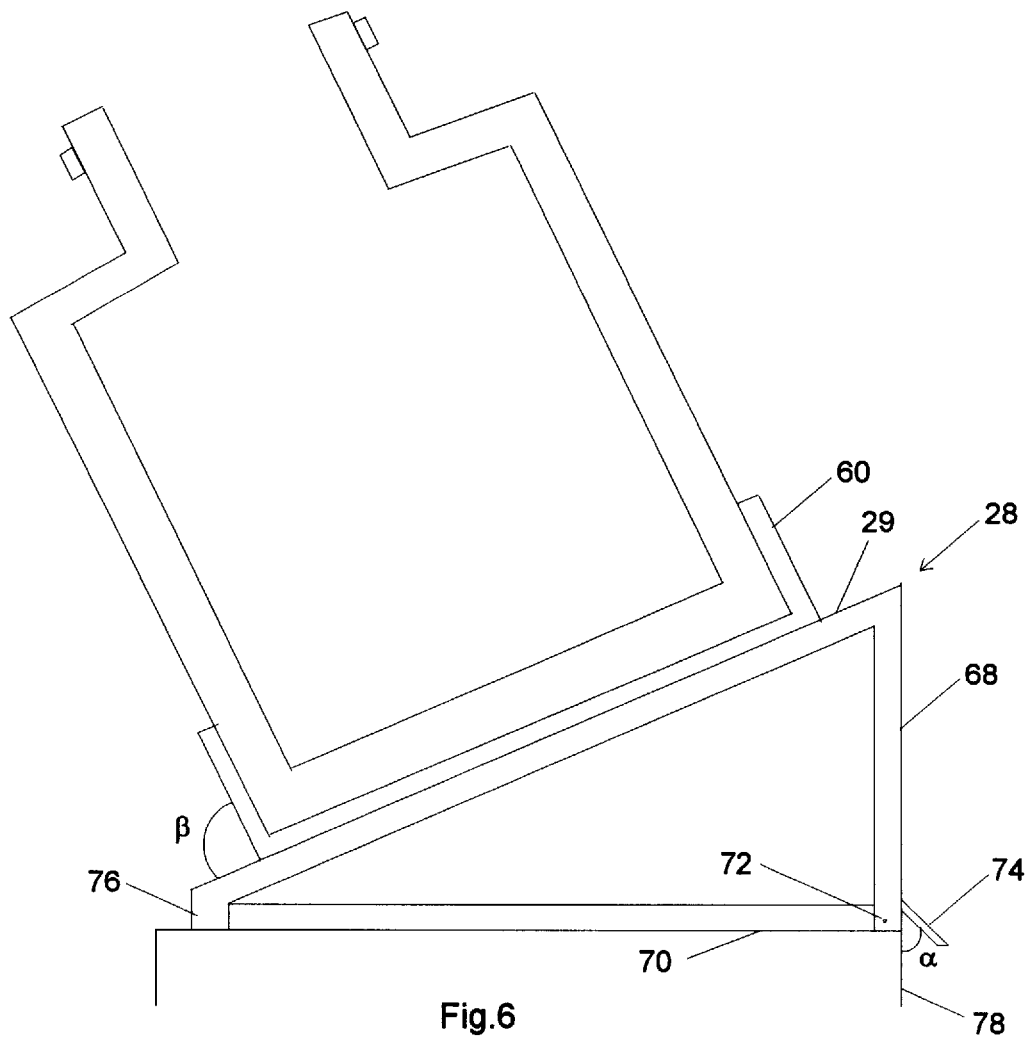
FIG. 6 is an alternative embodiment for the frame means used in the apparatus of the present invention for providing the chambers to be pivotally secured thereto.

Alternatively, the chambers can be pivoted from an acute angle, with respect to frame means, to a right angle, with respect to the frame means via a conventional pivot means. An example of such a pivot means is illustrated in FIG. 6. As seen, the supporting means 28 includes a triangular shape having a first leg 68 pivotally secured to a second leg 70 via a conventional pivot pin 72. The base 29 is located between the first leg and the second leg to provide for the triangular shape. A stop 74 extends downwardly and outwardly from the first leg 68. This stop 74 is disposed at an angle $\alpha$. The cup member 60 is secured to the attaching means at angle $\beta$. Thereby, the summation of angles $\alpha$ and $\beta$ will be equal to 90 degrees. For an acute positioning, the inner end of the base includes a downward extension 76. In the angular position (acute angle), the extension 76, as illustrated rests on frame means 14. For vertical position of the chambers, the users lifts extension 76 of the base 29. The stop 74 will terminate movement upon abutment with the rear portion 78 of the frame means 14. This will provide for the apparatus to be in a fixed and secured position, rendering the chambers to be located vertically with respect to the frame.

The apparatus can be re-configured to allow the user to alter from a vertical position to an acute position by utilizing a conventional adjustable tension lid support, such as the one manufactured by NATIONAL®. This embodiment is illustrated in further detail in FIGS. 7 and 8. As seen in these figures, the first leg and second leg are eliminated. The base 29 is secured to the frame means by conventional hinges 80. Located on opposite sides of the base and between the base 29 and frame means 14 is a conventional adjustable tension lid support 82 (illustrated and labeled in FIG. 8). This adjustable lid support will support the base at any angular position $\phi$. Thereby, providing the user the option of vertical placement or angular placement.

As seen in FIG. 7, the apparatus of the present invention is at a vertical position. In FIG. 8, the apparatus is locked at an acute angle $\phi$. As seen in this figure, the lid support includes an upper plate 84 and a lower plate 86. Secured to the upper and lower plate is lifting and securing element 88. This element will enable the apparatus to be in a locked and secured position when lifted, and also adapted to slide into the frame means when a vertical position is desired. The lower plate 86 includes an adjusting screw 90. The adjusting screw 90 is fixedly secured to the frame means. The central element 88 includes a groove 92. The adjusting screw 90 is received within this groove. Accordingly, providing for the element to slide upward to be in locked at an acute position (FIG. 8) or slide downward and be locked at a vertical position (FIG. 7). The acute angle $\phi$ can be changed and adjusted by moving the plate position.

While the invention has been particularly shown and described with reference to an embodiment thereof, it will be understood by those skilled in the art that various changes in form and detail may be made without departing from the spirit and scope of the invention.

We claim:

1. An apparatus to maintain, expand, and detect pinhole voids in elastomeric gloves, said apparatus comprising:
at least two hollow and empty chambers having an enclosed bottom and an open top;
said at least two chambers are constructed from a single layer of material;
said at least two chambers are secured to a frame means;
a vacuum means is coupled to said at least two chambers;
said vacuum means-includes a vacuum pump and said vacuum pump provides a vacuum when activated; and
said vacuum means operates each chamber to provide for each chamber to function independently to and separately from each other to enable a vacuum to remain in one chamber even if a vacuum is broken in a separate chamber.

2. An apparatus as in claim 1 wherein said frame means includes wheels for mobility.

3. An apparatus as in claim 1 wherein said vacuum pump and said vacuum means are enclosed and encased in a cabinet, said cabinet is located on said frame means.

4. An apparatus as in claim 3 wherein insulation is located interiorly within said cabinet for damping vibration and noise of said vacuum pump and said vacuum means.

5. An apparatus as in claim 1 wherein said vacuum means comprises a conduit to be coupled to each chamber and a check valve to be located within each conduit of each chamber, a separate conduit is coupled to said vacuum pump, said separate conduit includes a separate check valve, a conventional conduit connector couples each conduit of each chamber together, and said conventional conduit connector is coupled to said separate conduit.

6. An apparatus as in claim 1 wherein said at least two chambers are pivotally secured to said frame means.

7. An apparatus as in claim 1 wherein said at least two chambers are removably secured to said frame means via a removable means.

8. An apparatus as in claim 1 wherein a plurality of bumps are exteriorly located on each chamber.

9. An apparatus as in claim 1 wherein a cover is removably secured to said open top of each chamber when not in use.

10. An apparatus as in claim 1 wherein each chamber includes an upper section and a lower section, said upper section steps inward from said lower section to provide for said lower section to be larger than said upper section.

11. An apparatus to maintain, expand, and detect pinhole voids in elastomeric gloves, said apparatus comprising:
at least two hollow and empty chambers having an enclosed bottom and an open top;
said at least two chambers are constructed from a single layer of material;
said at least two chambers are secured to a frame means;
an access means for allowing each of said at least two chambers to be sterilized;
a vacuum means is coupled to said at least two chambers and, when activated, provide for a vacuum to be located within each chamber;
said vacuum means includes a vacuum pump and said vacuum pump provides a vacuum when activated;
said vacuum means operates each chamber to provide for each chamber to function independently to and separately from each other to enable a vacuum to remain in one chamber even if a vacuum is broken in a separate chamber;
a pivot means secures said at least two chambers to said frame means; and
said pivot means provides for said at least two chambers to be at an acute angle with respect to said frame means when in a first position and for said at least two chamber to be at a right angle with respect to said frame means when in a second position.

12. An apparatus as in claim 11 wherein said vacuum means are enclosed and encased in a cabinet, said cabinet is located on said frame means.

13. An apparatus as in claim 12 wherein insulation is located interiorly within said cabinet for damping vibration and noise of said vacuum pump and said vacuum means.

14. An apparatus as in claim 11 wherein a plurality of bumps are exteriorly located on each chamber.

15. An apparatus as in claim 11 wherein each chamber includes an upper section and a lower section, said upper section steps inward from said lower section to provide for said lower section to be larger than said upper section.

16. An apparatus to maintain, expand, and detect pinhole voids in elastomeric gloves, said apparatus comprising:
at least two chambers having an enclosed bottom and an open top;
said at least two chambers are secured to a frame means;
a vacuum means is coupled to said at least two chambers;
said vacuum means includes a vacuum pump and said vacuum pump provides a vacuum when activated;
said vacuum means operates each chamber to provide for each chamber to function independently to and separately from each other to enable a vacuum to remain in one chamber even if a vacuum is broken in a separate chamber;
a removable means removably secures said at least two chambers to said frame means for enabling said at least two chambers to be sterilized; and
said removable means provides for said at least two chambers to be removable from and replaceable to said frame means.

17. An apparatus as in claim 16 wherein each of said at least two chambers includes sidewalls which taper outwardly from said enclosed bottom to said open top for providing said at least two chamber to be stackable with each other.

18. An apparatus as in claim 16 wherein a plurality of bumps are exteriorly located on each chamber.

19. An apparatus as in claim 16 wherein each chamber includes an upper section and a lower section, said upper section steps inward from said lower section to provide for said lower section to be larger than said upper section.

20. An apparatus as in claim 16 wherein a base secures said removable means to said frame means, said base is pivotally secured to said frame means via a pivot means.

* * * * *